United States Patent [19]
Gaarslev

[11] Patent Number: 5,246,856
[45] Date of Patent: Sep. 21, 1993

[54] SPECIMEN RECEPTACLES FOR SWABBING SETS

[75] Inventor: Knud Gaarslev, Great Harwood, Great Britain

[73] Assignee: Scan-Labs Ltd., Great Harwood, Great Britain

[21] Appl. No.: 730,799

[22] PCT Filed: Jan. 26, 1990

[86] PCT No.: PCT/GB90/00108

§ 371 Date: Jul. 24, 1991

§ 102(e) Date: Jul. 24, 1991

[87] PCT Pub. No.: WO90/08817

PCT Pub. Date: Aug. 9, 1990

[30] Foreign Application Priority Data

Jan. 26, 1989 [GB] United Kingdom ................. 8901665

[51] Int. Cl.$^5$ ............................................. C12M 1/30
[52] U.S. Cl. ................................... 435/295; 435/294; 435/805; 422/58; 422/61; 422/102; 206/363; 206/438; 128/759; 604/1

[58] Field of Search ..................... 435/294, 295, 805; 628/759; 422/58, 61, 102, 99, 104; 604/1; 206/306, 438, 363

[56] References Cited

U.S. PATENT DOCUMENTS

| | | | |
|---|---|---|---|
| 2,768,736 | 10/1956 | Govoni | 206/306 |
| 3,776,220 | 12/1973 | Monaghan | 604/1 |
| 3,966,552 | 6/1976 | Pagano et al. | 435/294 |
| 4,184,483 | 1/1980 | Greenspan | 128/759 |
| 4,528,187 | 7/1985 | Truglio | 422/102 |

Primary Examiner—Robert J. Warden
Assistant Examiner—Krisanne M. Thornton
Attorney, Agent, or Firm—Biebel & French

[57] ABSTRACT

The invention relates to a specimen receptable (5) for a swabbing set, having reduced diameter swab compartment (3) at its lower end. When a swab device is inserted into the receptacle (5), and the upper end (6) of the receptacle is closed by a stopper (4) carried by the stick (1) of the swab device, the specimen-containing swab (2) is compressed by, and closely confined in, the compartment (3), to hinder the access of air to the specimen absorbed in the swab and thereby protect the specimen.

10 Claims, 1 Drawing Sheet

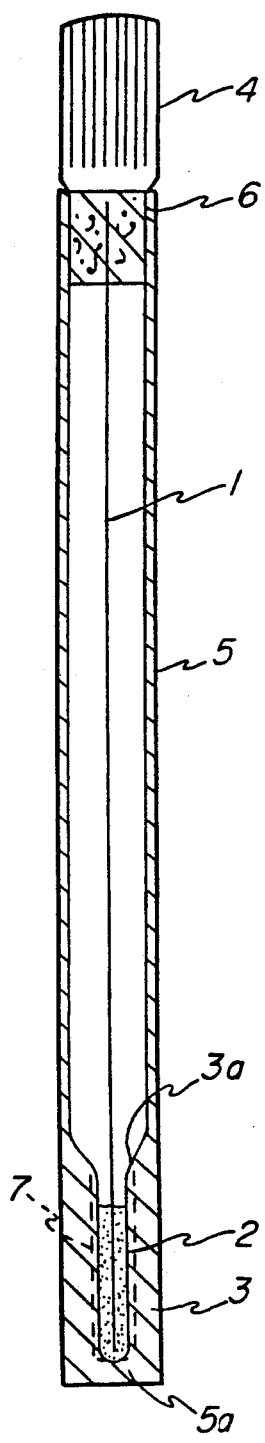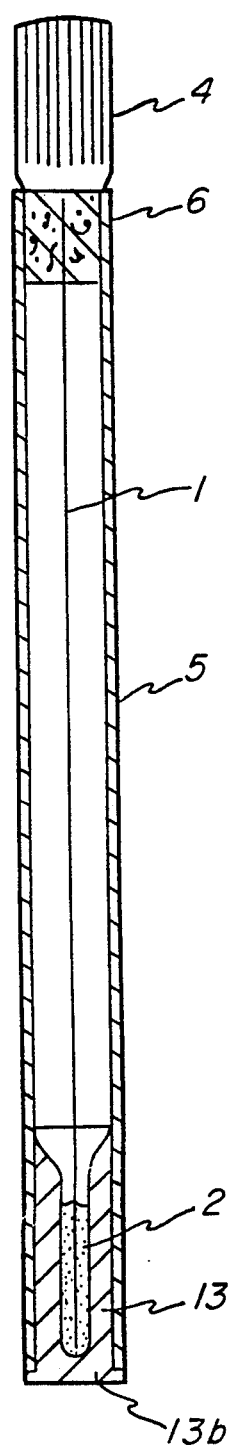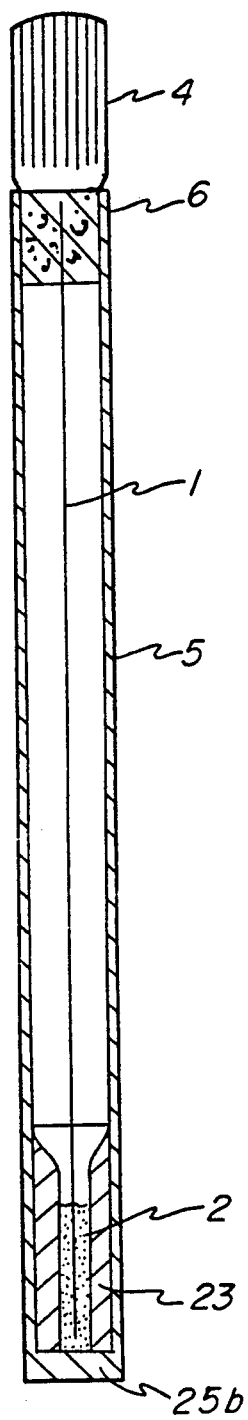

SPECIMEN RECEPTACLES FOR SWABBING SETS

The present invention relates to a specimen receptacle for use, for example, as part of a swabbing set for collection and transport of a specimen required for microbiological examination.

It is known to obtain specimens for microbiological examination by means of a swab stick which includes a swab of absorbant material which sucks up the specimen, which is located at one end of an elongate element, such as a stick or length of wire, by which the swab is handled and manipulated. The swab and absorbed specimen are transported to the laboratory where the examination is to be performed, either in a sterile, dry, closed receptacle in the form of a tube, or immersed in a sterile, watery, often partly solidified transport medium, in a similar closed tube. In the laboratory, the swab is removed from the tube, and the specimen is squeezed from the absorbent material and subjected to various procedures depending upon the specific purpose of the examination.

Although such specimen tubes are closed in an airtight manner, there is still a tendency for the specimens contained therein to deteriorate, and it is an object of the present invention to provide an improved specimen tube which significantly reduces this tendency.

According to one aspect of the present invention, there is provided a swabbing set including a specimen receptacle, and a swab device including an absorbent swab receivable in the receptacle, the receptacle having a region of reduced internal cross-section, and the absorbent swab, when the swab device is inserted into the receptacle in use of the latter, being received by said region of reduced internal cross-section, characterised in that the region of reduced internal cross-section defines an elongate swab compartment which contains, closely confines, and engages the swab when the swab device is inserted fully into the receptacle, to effectively isolate the sides and tip of the swab from air in the remainder of the receptacle and thereby hinder evaporation and oxygenation of a specimen when absorbed in the swab.

According to another aspect of the present invention, there is provided a specimen receptacle for use in a swabbing set as just defined the receptacle comprising a tube having an open end, a closed opposite end, and a region of reduced internal cross-section for receiving and closely surrounding an absorbent swab of a swab device, characterised in that the region defines a longitudinally extending swab compartment disposed at or adjacent the closed end and spaced from the open end, the swab compartment being elongate in the longitudinal direction of the tube, and having an internal cross-section which is smaller than that of the longitudinally extending region of the tube between the swab compartment and the open end, so that, when a swab device is inserted fully into the receptacle in use of the latter, the swab is contained in the swab compartment, and is closely confined by, and engaged by, the swab compartment, whereby the cooperation between the swab and swab compartment effectively isolates the sides and tip of the swab from air in the receptacle so as to hinder evaporation and oxygenation of a specimen absorbed in the swab.

In one embodiment, a swab device or stick comprises a swab of absorbent material mounted at one end of a stick or other elongate element, the other end of the elongate element being connected to a stopper for the receptacle. The receptacle is in the form of a tube, for example basically similar to a test tube. The tube is provided, adjacent its lower closed end, with a longitudinally extending region having an internal diameter which is less than that of the remaining upper portion of the tube. The cross-sectional area of the lower region of the tube approximates, or is less than, that of the swab when in an unrestrained condition. The relative lengths of the swab stick and tube are such that, when the swab stick is inserted into the tube to a position in which the stopper sealingly closes the open upper end of the tube, the swab enters the reduced-diameter region, and is closely confined and also preferably compressed therein.

This reduced-diameter region provides a tight fitting compartment which acts as a protection against loss of viability of the micro-organisms in the specimen absorbed in the swab, because the close confinement of the swab effectively isolates the sides and tip of the swab from the air in the tube above the compartment, significantly hindering evaporation and oxygenation of the specimen absorbed in the swab. In addition, any dissolved, protective compounds which may have initially dried up in absorbent material of the swab may be re-activated, for example squeezedout and re-associated with the micro-organisms.

Thus, survival of cell structures and micro-organisms during transport is achieved, making detection of the latter in the laboratory possible.

In order that the invention may be more readily understood, reference will now be made to the accompanying drawings, in which:

BRIEF DESCRIPTION OF THE DRAWINGS

FIG. 1 is a diagrammatic side view of a swabbing set according to a first embodiment of the invention; and FIGS. 2 and 3 are similar views of alternative embodiments of the invention.

Referring to the FIG. 1, a swab device comprises a swab 2 of absorbant material, such as specially prepared cotton or cotton-like material, cotton wool, etc., or a porous plastics sponge material such as polyethylene, etc., which is attached to, for example wound around, one end of an elongate element or carrier 1 of wire, plastics material, wood or rolled up paper, etc. To the other end of the carrier 1 is attached a closure member or stopper 4, for example of resilient plastics material, which is intended to sealingly cooperate with the upper end 6 of a specimen receptacle or container in the form of a tube 5. The stopper 4 also serves as a handle by which the swab is intended to be handled and manipulated.

The lower closed end of the specimen tube 5 is provided with a longitudinally extending region 3, the internal diameter of which is less than that of the remaining upper region of the tube 5. The upper end of the region 3 terminates in an inverted conical guide surface 3a. The region 3 defines a compartment for receiving and closely confining the swab 2 when the swab The swab 2 in its free or unconfined state prior to insertion into the compartment 3, preferably has a cross-sectional area which generally approximates, or is greater than, that of the compartment 3. Thus, when the swab 2 is inserted longitudinally into the compartment 3 as shown, it is closely or tightly surrounded by the sides of the compartment, and may also be slightly compressed between the sides, and engages or is adjacent the bottom of the compartment. Thus, as will be apparent from the figure, the swab, and the specimen and/or protective compound(s), etc, with which the swab is impregnated will be effectively isolated from the air in the region of the tube 5 above the compartment 3. This isolation may be effected or enhanced by the formation of a bead of liquid above the swab in the compartment squeezed out of the swab due to its compression in the compartment. The conical or curved upper end of the compartment forms a gentle lead-in or guide surface for the swab as it enters the compartment.

In one specific and non-limiting example, the elongate element or carrier 1 of the swab device is made of wood, plastics material or metal, and has a thickness or diameter of approximately 1 mm. The swab of absorbant material may be of the order of 3 to 6 mm. and preferably 4 to 5 mm. thick, and 15 to 25 mm. long. The tube 5 may be manufactured from glass, metal or a plastics material. The swab compartment or region 3 may have an internal diameter of the order of 3 mm. to 6 mm. and a length of the order of 20 to 30 mm. However, the proportions, dimensions and/or materials may be changed.

In the embodiment of FIG. 1, the region or compartment 3 is an integral part of the tube 5, and the lower end of the tube 5 is closed by an integral, transverse end wall 5A. However, as shown in FIG. 2 or 3, the region or compartment may alternatively be defined by a preformed member, for example an insert 13 (FIG. 2) or 23 (FIG. 3) in the form of a tube or sleeve which may be molded or otherwise formed from a plastics material, or glass. The insert may be press fitted into the bottom of the tube, and/or may be anchored in other ways, for example by an adhesive. As shown in FIG. 2, the bottom of the compartment in the insert 13 may be closed by an integral, transverse wall 13b. Alternatively, as shown in FIG. 3, the bottom of the compartment in the insert 23 may be defined by the bottom 25b of the tube.

It will be understood that various modifications may be made without departing from the scope of the present invention.

The specimen receptacle is primarily intended to be disposable, i.e. used once and then discarded. For this reason, to minimise cost, it is envisaged that it will be preferable to employ conventional commercially available specimen tubes, fitted with preformed members or inserts defining the swab compartments as previously described with respect to FIG. 3. However, this is not essential, and, for example, the lower end of the tube may be open, and the preformed member or insert defining the swab compartment may be attached to the lower open end of the tube and close the latter. Alternatively, the compartment could be formed integrally with the tube by locally thickening the tube wall as described with respect to FIG. 2, or by necking-in the side wall of the tube without significantly increasing the thickness of the wall, or by a combination of the two.

The tube and/or the swab compartment may be other than circular in cross-section, and/or may be tapered or stepped in a longitudinal direction.

The swab compartment may, if required, extend by a greater distance up to the tube, and/or may be spaced from the bottom of the tube.

The specimen receptacle or container may be in the form of a bottle, vial, etc. instead of a tube, with the swab compartment or equivalent forming part of, or being attached to, the bottom of the receptacle, and, if required spaced from the side wall(s) of the receptacle.

Although primarily intended for use with microbiological specimens, the receptacle, and/or the associated swab or other device, could be employed to contain, store and/or transport other substances for medical or non-medical purposes.

The swab compartment may be formed with one or more longitudinally extending grooves in its interior side wall, indicated in broken lines at 7 in FIG. 1, which serve to assist in insertion and release of the swab. In particular, during insertion of the swab, the grooves serve to permit air trapped in the bottom of the compartment to escape, and/or allow air to enter beneath the swab during withdrawal.

The swab 2 and carrier 1 may be formed integrally. For example, the carrier may be formed from a plastics material which is capable of being expanded, and the tip of the carrier may be locally treated to gas or expand it to form it into a porous swab.

I claim:

1. A swabbing set comprising, in combination:
    a) a swab device comprising an elongate swab carrier having a swab of a compressible, absorbent material adjacent one end thereof, the swab having external side and tip surfaces; and
    b) a tubular, specimen receptacle within which the swab device is insertable, the receptacle having an open end, closed opposite end, a longitudinally extending swab compartment having an internal wall, and being disposed adjacent the closed opposite end, extending from the closed opposite end towards the open end, the swab compartment having an open, swab inlet end facing towards the open end of the receptacle and opening into a longitudinally extending region of the receptacle disposed intermediate the swab compartment and the open end of the receptacle and communicating with the open end of the receptacle, having a permanently closed end opposite said open, swab inlet end, and having an internal cross-section, over substantially its entire longitudinal extent between its open, swab inlet end and its permanently closed end, which is less than that of the intermediate region, and which is not greater than a cross-section of the swab when in its free, unconfined state prior to insertion into the swab compartment, the swab compartment being constructed such that, when the swab device is inserted fully into the receptacle, the swab, over at least a major proportion of its length, is contained in, closely confined by, and engaged by the internal wall of the swab compartment, whereby the cooperation between the swab and the internal wall of the swab compartment effectively isolates the side and tip surfaces of the swab from air in the receptacle so as to hinder evaporation and oxygenation of a specimen absorbed in the swab.

2. A swabbing set as claimed in claim 1, wherein the receptacle and swab are in a dry, sterile condition prior to use.

3. A swabbing set as claimed in claim 1, wherein the swab is impregnated with at least one compound for protecting a specimen when absorbed by a swab, the compound being in a dry condition in the swab prior to use.

4. A swabbing set as claimed in claim 1, wherein the swab compartment is of circular internal cross-section.

5. A swabbing set as claimed in claim 4, wherein the swab compartment is bounded by a concave guide surface at its open swab inlet end.

6. A swabbing set as claimed in claim 4, wherein the swab compartment further comprises a synthetic plastics insert fitted to the receptacle at the closed opposite end thereof.

7. A swabbing set as claimed in claim 6, wherein the insert is closed by an end wall at its end remote from the open end of the receptacle, and wherein the insert is press fitted to the receptacle whereby the end wall of the insert also forms the closed opposite end of the receptacle.

8. A swabbing set as claimed in claim 6, wherein the swab compartment extends through the insert, and is closed by an end wall of the receptacle.

9. A swabbing set as claimed in claim 1, wherein the swab compartment has an internal side wall which is formed with one or more grooves for the passage of air during longitudinal insertion or removal of a swab.

10. A swabbing set as claimed in claim 1, wherein the end of the elongate carrier of the swab device remote from the swab is attached to a combined closure and handle member, the member being sealingly cooperable with the open end of the receptacle when the carrier is fully inserted into the receptacle and the swab is confined within the swab compartment.

* * * * *